US005534026A

United States Patent [19]
Manders et al.

[11] Patent Number: 5,534,026
[45] Date of Patent: Jul. 9, 1996

[54] PREPARATION OF INEXPENSIVE, HIV-FREE HUMAN SKIN ALLOGRAFT

[75] Inventors: Ernest K. Manders, Hummelstown; Andrea M. Koegel, Middletown; Donald R. Mackay, Hershey, all of Pa.

[73] Assignee: The Penn State Research Foundation, University Park, Pa.

[21] Appl. No.: 862,141

[22] Filed: Apr. 2, 1992

[51] Int. Cl.$^6$ ..................................... A61F 2/10
[52] U.S. Cl. ................... 623/15; 623/66; 623/11
[58] Field of Search ................. 623/15; 422/22

[56] References Cited

U.S. PATENT DOCUMENTS

| | | | |
|---|---|---|---|
| 3,645,849 | 2/1972 | Gray | 195/62 |
| 3,743,480 | 7/1973 | Falk | 21/2 |
| 4,347,841 | 9/1982 | Benyó et al. | 424/445 |
| 4,351,091 | 9/1982 | Goodkin | 27/22 |
| 4,361,552 | 11/1982 | Baur et al. | 424/445 |
| 4,880,512 | 11/1989 | Cornelius et al. | 204/157 |
| 4,897,260 | 1/1990 | Ross et al. | 424/97 |
| 4,959,211 | 9/1990 | Lombardo et al. | 424/93 |
| 4,994,237 | 2/1991 | Login et al. | 422/21 |
| 5,015,584 | 5/1991 | Brysk | 435/240 |
| 5,135,915 | 8/1992 | Czarniecki et al. | 435/240.1 |

OTHER PUBLICATIONS

The Molecular Basis of Cancer pp. 73–76 edited by Farmer and Walker (1985).
Young et al., "Stored Skin Homografts in Extensively Burned Patients" *Arch. Surg.*, vol. 80, Feb., pp. 208–213, 1990.
Dingman et al, "Coastal Cartilage Homografts Preserved by Irradiation", *Plastic & Reconstructive Surgery*, vol. 28, No. 5, Nov. 1961, pp. 562–566.
Rappaport et al, "Early Use of Xenografts as a Biologic Dressing in Burn Trauma", *The American Journal of Surgery*, vol. 120, pp. 144–148, 1970.
Wright et al, "Cooperative Studies in the Use of Ionizing Radiation for Sterilization and Preservation of Biological Tissues", *Sterilization and Preservation of Biological Tissues by Ionizing Radiation (International Atomic Energy Agency)*, pp. 107–120, 1970.
Graham et al "Versatility of Skin Allografts: Desirability of a Viable Frozen Tissue Bank", *The Journal of Trauma*, vol. 11, No. 6, pp. 494–501, 1971.
Ballantyne et al, "An Experimental Evaluation of Skin Graft Preservation with Silicone Fluid", *Cryobiology*, Oct. 8, pp. 211–215, 1971.

Korlof, "Radiation–Sterilized Split Skin: A New Type of Biological Wound Dressing", *Scandinavia Journal of Plastic Reconstructive Surgery*, vol. 6, pp. 126–131, 1972.
Colvard et al "Sterilization of Scleral Homografts with Ionizing Irradiation", *American Journal of Ophthalmology*, vol. 87, pp. 494–496, 1979.
Basile, "A Comparative Study of Glycerinized and Lyophilized Porcine Skin in Dressings for Third Degree Burns", *Plastic and Reconstructive Surgery*, pp. 969–972. Jun. 1982.
Pruitt et al, "Characteristics and Uses of Biologic Dressings and Skin Substitutes", *Arch. Surg.*, vol. 119, pp. 312–322, 1984.
Spire, "Inactivation of Lymphadenopathy–Associated Virus by Heat. Gamma Rays, and Ultraviolet Light," *The Lancet*, Jan. 26, 1985, pp. 188–189.
Clarke, "HIV Transmission and Skin Grafts", *The Lancet*, Apr. 25, 1987, p. 983.
Hermans, "Clinical Experience with Glycerol–Preserved Donor Skin Treatment In Partial Thickness Burns", *Burns*, vol. 15, No. 1, pp. 57–59, 1989.
Kreis et al, "The Use of Non–Viable Glycerol–Preserved Cadaver Skin Combined with Widely Expanded Autografts in the Treatment of Extensive Third–Degree Burns", *Journal of Trauma*, vol. 9, No. 1, pp. 51–54 1989.
Kitchen et al, "Effect of Gamma Irradiation on the Human Immuno–Deficiency Virus and Human Coagulation Proteins", *Vox Sang*, vol. 56, pp. 223–229, 1989.
Conway et al, "Radio Sensitivity of HIV–A—Potential Application To Sterilization of Bone Allografts", *AIDS*, 1991, vol. 5, No. 5, pp. 608–609.
Hiemstra et al, "Inactivation of Human Immunodeficiency Virus by Gamma Radiation and its Effect on Plasma and Coagulation Factors", *Transfusion*, vol. 31, No. 1, pp. 32–39, 1991.
Conway et al, "Radiosensitivity of Human Immunodeficiency Virus Type I", *Clinical Infectious Diseases*, vol. 14, Apr. 1992, pp. 978–979.

*Primary Examiner*—Jyothsna Venkat
*Attorney, Agent, or Firm*—Thomas J. Monahan

[57] ABSTRACT

A new method for the preparation and sterilization of skin allografts is presented. Human skin allografts are radiated in the present invention and applied as a temporary wound dressing on a graft dome. The invention is particularly useful for wound and burn therapies and presents a low cost, safe, and effective treatment that can be widely used with extensive storage capability.

5 Claims, No Drawings

PREPARATION OF INEXPENSIVE, HIV-FREE HUMAN SKIN ALLOGRAFT

BACKGROUND OF THE INVENTION

This present invention relates to a new method to prepare and sterilize human skin allografts for use as biological dressings. This method has applications in wound and burn therapy.

By way of background, allograft skin has been shown to provide an excellent temporary skin coverage for burn patients, acting as a biological dressing. Allograft skin protects the wound from desiccation, contamination, and decreases wound pain. When allograft skin shows general adherence to a burn wound and evidence of graft vascularization within 48 to 72 hours of application, one can anticipate an excellent take of autograft skin applied to the wound following removal of the allograft skin. Limitations of fresh allograft skin includes the dearth of material, the need for refrigerated storage facilities, and a limited "effective" shelf life of approximately seven to ten days when the tissue is stored at 4 degrees Celsius. The possibility of disease transmission requires careful donor selection [Pruitt, B A et al., *Arch. Surg.* 119, 312–322, (1984)].

Current developments in the field of allograft skin products focus on culturing epidermal cells to form skin-like coverings to be used as skin allografts as referenced in U.S. Pat. No. 5,015,584. Cryopreservation of allograft is commonly used, which retains the viability of the donor cells to some extent. It was previously believed that living cells were required for the success of skin allograft. However, good results have been obtained using methods which preserve the allograft without retaining the viability of the cells, such as preservation with glycerol [Kreis R W, et al., *J. Trauma* 29(1), 51–54 (1989)] [Hermans, M H E, *Burns* 15(1), 57–59 (1989)], silicone fluid [Ballantyne, D L Jr. et al., *Cryobiology* 8, 211–215, (1971)] or lyophilization [Young, J M et al., *Arch. Surg.* 80(Feb.), 208–213, (1960)].

Fresh-frozen allograft skin and lyophilized allograft skin have limitations such as demanding processing procedures. The requirements for such procedures confine the preparation of either material to special centers having proper facilities. The lyophilized material has an essentially unlimited nonrefrigerated shelf life, while the frozen material has a similarly prolonged shelf life provided proper refrigeration is maintained. Either material can be easily and rapidly prepared for use by rehydration or thawing. Lyophilized allograft skin generally adheres less well to the wound and is less able to reduce the bacterial count on the wound surface than fresh allograft skin [Pruitt, B A et al., *Arch. Surg.* 119, 312–322, (1984)].

U.S. Pat. Nos. 3,645,849 and 3,743,480 describe processes for of sterilization of biological material (e.g., blood serum) by microwave irradiation. Methods for preparing and sterilizing biological tissues such as heart valves, veins, cartilage, ligaments and organs for use as bioprostheses are described in U.S. Pat. No. 4,994,237. The source of irradiation is a microwave oven. This method tends to heat the specimen and destroy its structure. A method of sterilization of biological material by ultraviolet light is described in U.S. Pat. No. 4,880,512. Ultraviolet light is an efficient method of sterilization but it does not penetrate through objects such as skin very well. Consequently, this method is not always secure. In addition, Ultraviolet Light is not efficient for batch sterilization.

Another widely used method of biological tissue preservation and sterilization, which does not retain cell viability, is gamma irradiation. This method has been used extensively in the preservation of bone allograft, with good results. It has also been used in the preservation of donor cartilage [Dingman R O et al., *Plast. Reconstr. Surg.* 28(5), 562–567, (1961)], blood vessels, heart valves [Wright K A et al., *Sterilization and Preservation of Biological Tissues by Ionizing Radiation. Vienna, International Atomic Energy Agency,* 107–118, (1970)], dura mater, and sclera [Colvard D M et al., *Am. J. Ophthal.,* 87(4), 494–496, (1979)]. Irradiation sterilization of the tissue permits storage at room temperature, a considerable advantage when low temperature storage is unavailable. U.S. Pat. No. 4,351,091 employs gamma and x-ray irradiation to preserve a corpse to kill bacteria and other microorganisms that contribute to the decomposition of a corpse. This patent does not address infectious diseases such as viruses or the feasibility of preparing or preserving the corpse for organ donation.

With the use of allograft skin, there is an associated risk of the transmission of disease, including the human immunodeficiency virus (HIV). Skin banks around the world were virtually closed down for two or more years after the reported transmission of HIV from allograft skin [Clarke J A, *Lancet* 1,983, (1987)]. Gamma irradiation at ranges of 250,000 cGy to 2.5 million cGy has been shown to inactivate HIV [Hiemstra H et al., *Transfusion,* 31(1), 32–39, (1991)] [Spire B et al., *Lancet,* 1, 188–189, (1985)]. The effect of gamma irradiation on human coagulation factors found in human plasma and on virus suspended in plasma or other types of suspending medium has been studied [Kitchen, A D et al., *Vox Sang* 56, 223–229, (1989)].

The present invention overcomes the above-described disadvantages inherent with various materials and methods of the prior art.

SUMMARY OF THE INVENTION

In accordance with the present invention, a new method for the preparation and sterilization of human skin allografts is presented. Gamma irradiation has been earlier shown to inactivate HIV and has been used previously to sterilize allografts of bone and other tissues, but has not previously been used to sterilize and store the allograft skin at room temperature. Human skin allografts were irradiated in the present invention and applied as a temporary wound dressing on a skin graft donor site. When compared with a frozen skin allograft on the same recipient, the irradiated allograft proved to be as effective. This invention will be particularly useful for wound and burn therapies. It offers the potential of a low cost, safe and effective treatment that can be used widely and without extensive training or extensive facilities.

OBJECTS OF THE INVENTION

An object of this invention is to develop a method of sterilizing and storing human allograft skin so that the risk of transmission of infectious diseases, particularly viral diseases, is eliminated.

An additional object of this invention is to provide a method of preparing human allograft skin that is inexpensive and easily available to a large percentage of the medical community.

Another object of this invention is to allow for the preservation of sterile skin allografts without the need for refrigeration or other treatment which would result in additional expense.

Advantages of the present invention over the prior art and a better understanding of the invention and its use will become more apparent from the following disclosure.

DETAILED DESCRIPTION OF THE INVENTION

A detailed embodiment of the present invention is herein disclosed. However, it is understood that the disclosed preferred embodiment is merely illustrative of the invention that may be embodied in various forms. Accordingly, specific structural and method details disclosed herein are not to be interpreted as limiting, but merely as support for the invention as claimed and as a representative example for teaching one skilled in the art to variously employ the present invention.

The present invention describes the first known use of gamma irradiation to sterilize and prepare skin allograft for use as a biological dressing. Because of the risk of the transmission of infectious diseases such as HIV, hepatitis, and other viral diseases, the use of a safe, effective and inexpensive method has become apparent.

Donor skin from an HIV and hepatitis negative donor was obtained from the skin removed during a thighplasty. This skin was harvested using a power dermatome and sheets of skin 0.014 in. thick were obtained. These were placed immediately in Tis-u-Sol (Baxter; Deerfield, Ill.), a balanced salt solution, and stored overnight at 4 degrees Celsius. The harvested skin was then rinsed three times in Tis-u-Sol, and divided into several groups. One sample was placed in a solution of Eagles Minimal Essential Medium and dimethyl sulfoxide (DMSO) and frozen in liquid nitrogen. One piece was placed directly in formalin, to serve as a control for histological studies. Other pieces were placed in Tis-u-Sol in glass or plastic containers for irradiation with 3.0 million cGy at 23 degrees Celsius using a Cobalt-60 source. The invention can be practiced by irradiating skin samples for a period of time sufficient to provide a sterilizing dose of gamma radiation. Accordingly, such dosage is calculated using ordinary and usual parameters (i.e., medium size, etc.) of dosimetry. Irradiation dosages, sufficient to effect sterilization, are known in the art. Rinsing is not obligatory to practice the invention. As additional controls, several pieces of skin were left in Tis-u-Sol at 23 degrees Celsius both with and without antibiotics (5000 U/cc penicillin and 5000 mcg/cc streptomycin) for the amount of time required to irradiate the 3 million cGy samples. At the end of the irradiation period, a sample of the irradiated skin and a sample of each of the 23 degrees Celsius controls were cultured and placed in formalin for analysis. The remainder of the irradiated skin was stored at 23 degrees Celsius (room temperature) in the closed containers employed for the sterilization procedure and may be stored for an extended period of time.

After 14 days a sample of cryopreserved skin and two samples of the 3 million cGy irradiated skin were placed on a thigh skin graft donor site of a healthy volunteer. A portion of each allograft was placed in formalin for analysis at the time, and 2 mm punch biopsies were obtained at 3, 6, 8, 10, 13, 17, and 24 days post-op. All samples were stained using hematoxylin and eosin, as well as colloidal iron, and all histological samples were numbered and evaluated in a blinded fashion.

Cultures were negative for bacteria for both the control samples and the irradiated samples.

Throughout the study, the patient reported minimal pain from all areas of his donor site; no evidence of infection was seen at any time.

The clinical course of the allografts showed that at postoperative day two, both grafts looked somewhat pink and were firmly adherent to the graft bed. At day three both grafts were still pink and intact, but some epidermolysis was visible on the frozen allograft. By postoperative day six, the superficial epidermis of the frozen allograft had almost completely sloughed, while in contrast the irradiated allograft remained intact and supple. Histological examination at this point shows the frozen allograft dermis overlying the patient's own epidermis and dermis, while the irradiated graft appears intact but with nonviable cells. Between postoperative day eight and thirteen, the frozen allograft began to develop some areas of epitheliazation over the remaining allograft dermis, while the irradiated allograft began to form a thin eschar interspersed with some areas of epithelialization. By postoperative day seventeen the frozen allograft began to slough completely, while the site of the irradiated allograft was predominantly epithelialized, with some areas of eschar still remaining. Histologic examination shows the frozen allograft to be well epithelialized over the allograft dermis, with the patient's dermis and epidermis underneath; while the nonviable cells of the irradiated graft have been replaced with living cells. At postoperative day 27 the frozen allograft site still had many areas lacking epithelialization due to islands of retained allograft dermis, while the irradiated site was predominantly epithelialized.

We have shown that irradiated allograft is as effective a biological dressing as conventional frozen allograft. HIV and other viruses are inactivated by the radiation dose used in the present invention.

The results in this patient indicate that the cryopreserved allograft does indeed survive to form a viable skin layer over the patient's own tissue until it is rejected. The irradiated allograft forms an inert, protective barrier which sloughs after regrowth of the patient's own epidermis. Both forms of allograft performed well as a dressing, providing good coverage and pain relief as well as protection from infection. The irradiated allograft, however, produced a stable epithelial surface ten days before the cryopreserved allograft.

Skin allograft preservation by gamma irradiation has many advantages, and makes skin allograft use a possibility in areas where it is not currently available, such as small hospitals, doctors' offices, and developing countries of the world. The preparation of irradiated skin allograft is inexpensive and simple to perform, requiring only basic materials and access to a Cobalt-60 source. Irradiated allograft can be stored on the shelf at room temperature and does not require liquid nitrogen or low temperature freezer storage. Application of irradiated skin requires no thawing, washing or rehydration, as found with other methods of skin preservation.

The only factors limiting the usefulness of this technique are the availability of cadaveric skin and a Cobalt-60 source. The low cost of the method and the fact that the skin is virus-free, and specifically HIV-free, will make this a most attractive means of preparing allograft skin for patients with burns and other wounds.

Thus is described our invention and the manner and process of making and using it in such full, clear, concise and exact terms so as to enable any person skilled in the art to which is pertains, or with which it pertains, or with which it is most nearly connected, to make and use the same.

What is claimed is:

1. The method of preparing and storing a biologically sterile and virus-free skin allograft, comprising the steps of:

a) harvesting human skin from a donor to form a sheet of human skin allograft;

b) placing the sheet of skin allograft in contact with saline solution;

c) placing the sheet of skin allograft in a closed container;

d) exposing the closed container and confined sheet of skin allograft to a source of gamma radiation in an amount sufficient to sterilize the sheet of skin allograft and deactivate viruses in the sheet of skin allograft and render the skin allograft non-viable, and then removing the closed container and sheet of skin allograft from the source of irradiation; and e) storing the closed container and confined sheet of skin allograft at a temperature above freezing without degradation of the sheet of skin allograft while maintaining sterility and vital deactivation of the sheet of skin allograft.

2. The method of claim 1 including the step of:

f) performing step e) at room temperature.

3. The method of claim 1 including the steps of:

g) opening the container;

h) removing the sheet of skin allograft from the container; and i) then applying the sheet of skin allograft to a wound site on the body of a patient to form a biological dressing.

4. The method of claim 3 including the step of:

j) performing steps h) and i) without washing or rehydration of the sheet of skin allograft.

5. The method of claim 4 including the step of:

k) performing step d) by irradiating the sheet of skin allograft by exposure to approximately $3 \times 10^6$ cGy of cobalt-60 gamma radiation.

* * * * *

UNITED STATES PATENT AND TRADEMARK OFFICE
CERTIFICATE OF CORRECTION

PATENT NO. : 5,534,026
DATED : July 9, 1996
INVENTOR(S) : Ernest K. Manders

It is certified that error appears in the above-identified patent and that said Letters Patent is hereby corrected as shown below:

<u>Title page,</u>
Item [75], Inventors, "Andrea M. Koegel" and "Donald R. Mackay" should be deleted.

Signed and Sealed this

Sixteenth Day of May, 2006

JON W. DUDAS
*Director of the United States Patent and Trademark Office*